(12) United States Patent
Takayama et al.

(10) Patent No.: US 7,470,897 B2
(45) Date of Patent: Dec. 30, 2008

(54) NUCLEAR MEDICAL APPARATUS

(75) Inventors: Takuzo Takayama, Otawara (JP); Katsuhiko Fujimoto, Saitama (JP); Shigeharu Ohyu, Yaita (JP); Yasuo Sakurai, Otawara (JP); Mariko Shibata, Yokohama (JP); Atsuko Sugiyama, Nasushiobara (JP); Keisuke Hashimoto, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/671,233

(22) Filed: Feb. 5, 2007

(65) Prior Publication Data

US 2007/0194222 A1     Aug. 23, 2007

(30) Foreign Application Priority Data

Feb. 8, 2006    (JP)    ............................. 2006-031414

(51) Int. Cl.
G12B 13/00    (2006.01)
(52) U.S. Cl. .................................. 250/252.1
(58) Field of Classification Search ............... 250/252.1
See application file for complete search history.

(56) References Cited

U.S. PATENT DOCUMENTS

| 6,175,116 B1 | 1/2001 | Gagnon et al. |
| 6,175,118 B1 | 1/2001 | Takayama et al. |
| 2003/0108147 A1 | 6/2003 | Kojima et al. |

FOREIGN PATENT DOCUMENTS

| DE | 1 564 483 | 4/1971 |
| EP | 0 221 653 A2 | 5/1987 |
| JP | 11-38145 | 2/1999 |
| WO | WO 9847103 A1 * | 10/1998 |
| WO | WO 2004/072679 A2 | 8/2004 |

OTHER PUBLICATIONS

P. Msaki, et al., "Normalization of Multispectral Data in Positron Emission Tomography", Physics in Medicine & Biology, XP 000417895, vol. 38, No. 12, Dec. 1, 1993, pp. 1745-1760.

* cited by examiner

*Primary Examiner*—David P Porta
*Assistant Examiner*—Mark R Gaworecki
(74) *Attorney, Agent, or Firm*—Oblon, Spivak, McClelland, Maier & Neustadt, P.C.

(57) ABSTRACT

A nuclear medical apparatus for obtaining a distribution of a radioisotope in a subject by administering to a subject a radioactive medicine labeled with a radioisotope, detecting gamma rays given off from the radioisotope in a gamma-ray detecting section and counting the detected gamma rays in a count section. A correcting section is provided to correct for a count taken at the count section, by use of collection efficiency data determined according to the gamma-ray detecting section and an energy the gamma rays possesses.

8 Claims, 12 Drawing Sheets

| COLLIMATOR TYPE / ENERGY (keV) | COLLECTION EFFICIENCY AT LOW-ENERGY GENERAL-PURPOSE COLLIMATOR | COLLECTION EFFICIENCY AT LOW-ENERGY HIGH-RESOLUTION COLLIMATOR | COLLECTION EFFICIENCY AT HIGH-ENERGY GENERAL-PURPOSE COLLIMATOR | COLLECTION EFFICIENCY AT HIGH-ENERGY HIGH-RESOLUTION COLLIMATOR |
|---|---|---|---|---|
| 10 | 0.87 | 0.77 | 0.99 | 0.99 |
| 20 | 0.83 | 0.74 | 0.98 | 0.97 |
| 30 | 0.79 | 0.7 | 0.94 | 0.93 |
| 40 | 0.75 | 0.66 | 0.9 | 0.89 |
| 50 | 0.71 | 0.62 | 0.86 | 0.85 |
| 60 | 0.67 | 0.58 | 0.82 | 0.81 |
| 70 | 0.63 | 0.54 | 0.78 | 0.77 |
| 80 | 0.59 | 0.5 | 0.74 | 0.73 |
| 90 | 0.55 | 0.46 | 0.7 | 0.69 |
| 100 | 0.51 | 0.42 | 0.66 | 0.65 |
| 110 | 0.47 | 0.38 | 0.62 | 0.61 |
| 120 | 0.43 | 0.34 | 0.58 | 0.57 |
| 130 | 0.39 | 0.3 | 0.54 | 0.53 |
| 140 | 0.35 | 0.26 | 0.5 | 0.49 |
| 150 | 0.31 | 0.22 | 0.46 | 0.45 |
| 160 | 0.27 | 0.18 | 0.42 | 0.41 |
| 170 | 0.23 | 0.14 | 0.38 | 0.37 |
| 180 | 0.19 | 0.1 | 0.34 | 0.33 |
| 190 | 0.15 | 0.06 | 0.3 | 0.29 |
| 200 | 0.11 | 0.02 | 0.26 | 0.25 |
| 210 | 0.07 | 0 | 0.22 | 0.21 |
| 220 | 0.03 | 0 | 0.18 | 0.17 |

NUCLEAR MEDICAL APPARATUS

CROSS-REFERENCE TO RELATED APPLICATIONS

This application is based upon and claims the benefit of priority from prior Japanese Patent Application No. 2006-031414, filed Feb. 8, 2006, the entire contents of which are incorporated herein by reference.

BACKGROUND OF THE INVENTION

1. Field of the Invention

The present invention relates to a nuclear medical apparatus capable of obtaining a three-dimensional distribution of a radioisotope in a subject by administrating the subject with a radioactive medicine labeled with the radioisotope and detecting the gamma rays given off from the radioisotope.

2. Description of the Related Art

There is known a single photon emission computed tomography (SPECT apparatus) as one of the nuclear medical apparatuses that, by administering a radioactive medicine labeled with a radioisotope to a subject, a distribution of the radioisotope in the subject is imaged from the distribution state of the gamma rays given off from the radioisotope. The SPECT apparatus is an apparatus that, by administering to a subject a radioisotope of $^{99m}$Tc, $^{201}$Tl, $^{123}$I or the like, (termed a single photon nuclide), to radiate one gamma ray upon collapse, and counting the gamma rays given off upon collapse of the administered radioisotope, photon by photon, at a body exterior, thereby reconstructing a tomographic image of the subject from a concentration distribution of the nuclide on a tomographic plane.

Of among the radioactive medicines labeled with radioisotopes, there are nuclides that give off a plurality of energies. It is known that, where collecting gamma rays from such a nuclide giving off a plurality of energies, the quality of a tomographic image can be improved by setting up a collection window at around the energy at which the count value of the gamma rays given off from the radioisotope to be measured (termed a peak energy) maximizes and by gathering only the gamma rays fallen within the collection window. Meanwhile, there is known, say, a triple energy window (TEW) scheme as one of scattering-ray corrections for the effect of scattering gamma rays fallen within the collection window (see JP-A H11-38145, for example). In this scheme, besides the main collection window, sub-collection windows are provided on the higher and lower sides than the main window so that the effect of scattering rays, upon the count value of the gamma rays in the main window, can be corrected from the count values of the gamma rays as counted in the two sub-windows.

In the SPECT apparatus, count can be simultaneously made on the radioisotopes respectively contained in a plurality of radioactive medicines. In such a case, collection windows are set up at around the peak energies respectively corresponding to the plurality of radioisotopes so that the gamma rays given off from the radioisotopes can be separated by individually gathering the gamma rays fallen within the collection windows established.

In the meanwhile, the radiation detector (e.g. structured by an NaI scintillator and a photoelectron multiplier) used on the SPECT apparatus has a collection efficiency different depending upon the energy of the gamma rays given off from the radioisotope. Collection efficiency is unique to the structure of the radiation detector wherein collection efficiency has a change ratio differing relying upon the gamma ray energy due to the type of a collimator arranged on the radiation detector.

In this situation, in the existing medical apparatus, the difference of energy-based collection efficiency is not corrected thus measuring higher-energy and lower-energy gamma rays equally one in count. The SPECT apparatus already possesses the function of storage in different files for the collection energy windows. Although it is conventionally possible to merely take reciprocals of the images of within the files, there encounters a problem in displaying, on the same image, the gamma rays gathered in different collection energy windows.

For example, where administering a radioactive medicine to a body interior and quantitating the administered radioactive medicine (measuring an integration site and quantity of the radioactive medicine) thereby quantitating a protein (e.g. an organ or a tissue) using the radioactive medicine, it is essentially required to correct for the gamma-ray count value by taking account of the effect of collection efficiency different from energy to energy and from collimator to collimator. Likewise, where administering a plurality of radioactive medicines to a body interior and simultaneously quantitating the plurality of administered radioactive medicines (measuring integration sites and quantities of the radioactive medicines), it is significantly important to correctly discriminate the gamma-ray based on the collection window in which the gamma rays are gathered. In such a case, it is essentially required to correct for the gamma-ray count value by taking account of the effect of collection efficiency different from energy to energy and from collimator to collimator.

Furthermore, when correcting for scattering rays according to the TEW scheme, correction is based on the gamma-ray count values concerning the collection windows provided around the main window. However, in the current situation, the energy-based and collimator-based differences of collection efficiencies are not reflected upon the sub-windows on the higher and lower energy sides than the main window.

BRIEF SUMMARY OF THE INVENTION

It is an object of the present invention to produce a more quantitative image by correcting for the count value of gamma rays through taking account of the energy-dependent difference of collection efficiency.

A nuclear medical apparatus in a first aspect of the invention is a nuclear medical apparatus for obtaining a distribution of a radioisotope in a subject by administering to a subject a radioactive medicine labeled with a radioisotope, detecting gamma rays given off from the radioisotope in a gamma-ray detecting section and counting the detected gamma rays in a count section, the apparatus characterized by: having a correcting section that corrects for a count taken at the count section, by use of collection efficiency data determined according to the gamma-ray detecting section and an energy the gamma rays possesses.

A nuclear medical apparatus in a second aspect of the invention is a nuclear medical apparatus comprising: a nuclear medical apparatus comprising: a gamma-ray detecting section that detects gamma rays given off from a radioisotope contained in a radioactive medicine administered to a subject and determining an incident site of the gamma rays and an energy the gamma rays possesses; a gamma-ray collecting section that gathers the gamma rays, in a case gamma rays detected at the gamma-ray detecting section have an energy fallen within a predetermined collection window; an output section that outputs a value commensurate with a collection efficiency of the gamma rays determined according to a type of the gamma-ray detecting section and an energy the gamma rays possesses; a gamma-ray count section that determines a count value of the gamma rays entered the gamma-ray detecting section depending upon the value commensurate with a collection efficiency outputted from the output section, in a case gamma rays are gathered in the gamma-ray collecting section; and a display section that displays an image based on the determined count value of gamma rays.

A nuclear medical apparatus in a third aspect of the invention is a nuclear medical apparatus comprising: a gamma-ray detecting section that detects gamma rays given off from radioisotopes different in energy peak and respectively contained in a plurality of radioactive medicines administered to a subject, and determines an incident site of the gamma rays and an energy the gamma rays possesses; a gamma-ray collecting section that gathers the detected gamma rays on each of the radioisotopes; and a display section that displays an image on each of the radioisotopes gathered.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

With reference to the drawings, explanations will now be made on embodiments according to the present invention.

FIRST EMBODIMENT

Figure 1:
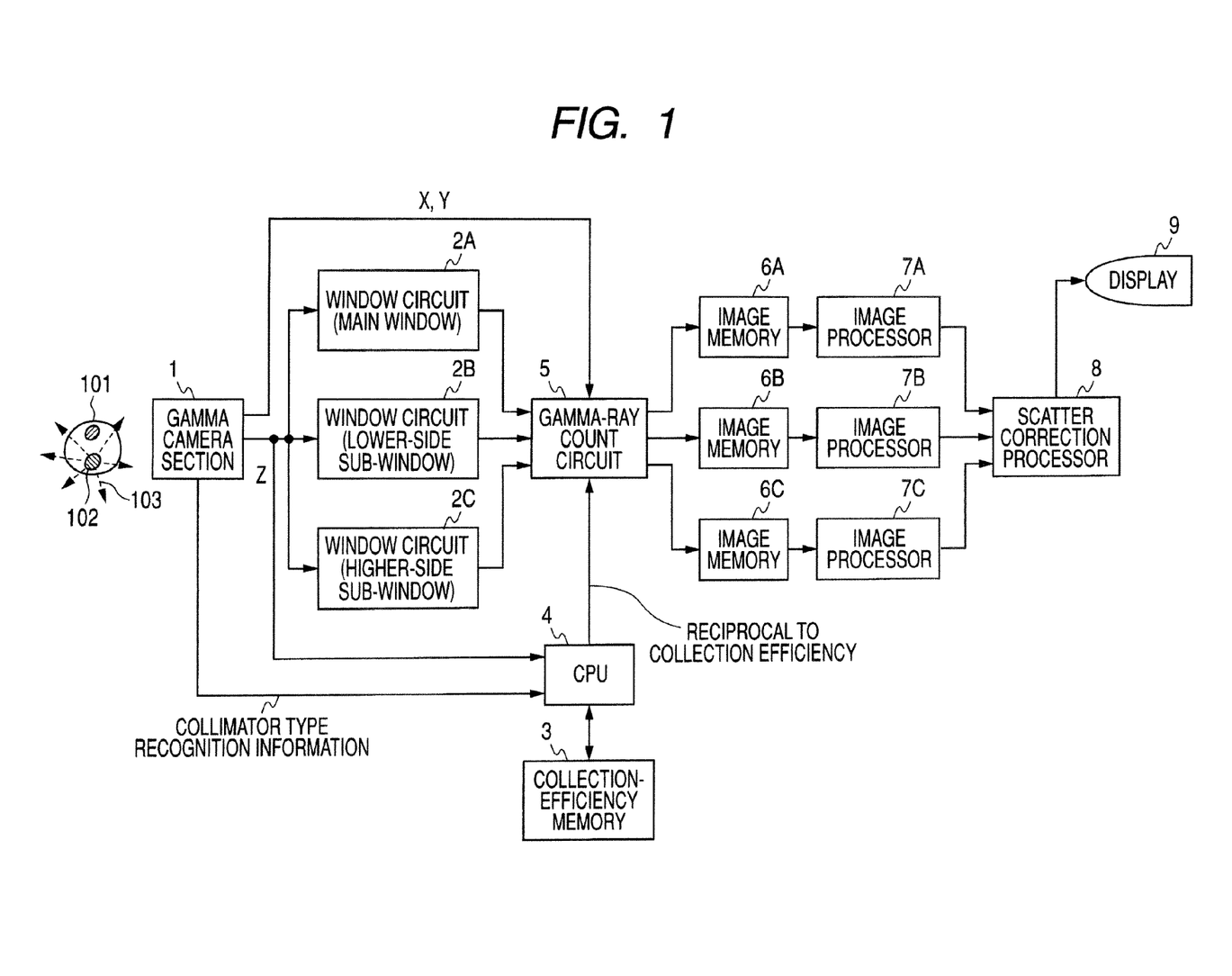
FIG. 1 is a diagram showing the main arrangement of a nuclear medical apparatus according to a first embodiment of the invention.

FIG. 1 is a diagram showing a main arrangement of a nuclear medical apparatus according to a first embodiment of the invention. The nuclear medical apparatus shown in FIG. 1 is constructed with a gamma camera section 1, window circuits 2A, 2B, 2C, a collection-efficiency memory 3, a CPU 4, a gamma-ray count circuit 5, image memories 6A, 6B, 6C, image processors 7A, 7B, 7C, a scatter-correction processor 8, and a display 9.

The gamma camera section 1 is to detect gamma rays (photons) 103 given off from a radioactive medicine 102 administered to a subject 101. The gamma camera section 1 may be an Anger gamma camera or a semiconductor-array gamma camera. The gamma camera if in the Anger type is structured with a collimator formed two-dimensionally with a plurality of parallel pores for regulating the incident direction of the gamma rays 103 radiated from the radioactive medicine 102 administered to the subject, a scintillator for absorbing the energy of the gamma rays 103 coming through the collimator and issues flash light at the relevant site, a plurality of photoelectron multipliers for converting the flash light from the scintillator into an electric signal, and a detecting circuit for detecting the incident site and energy of the gamma rays 103. Meanwhile, the gamma camera if in the semiconductor array type is arranged with a semiconductor element that receives the gamma ray 103 and generates an electric signal commensurate with the energy thereof, in place of the scintillator and the photoelectron multipliers.

Here, the collimator is removably arranged in gamma camera section 1 in the FIG. 1. The type of the collimator arranged in the gamma camera section 1 is notified as collimator recognition information (e.g. collimator's ID number, etc.) to the CPU 4. The collimators, to be arranged on the gamma camera section 1, include various types, e.g. a collimator for low energy or for high energy can be used depending upon the energy of the gamma rays given off from the radioisotope contained in the radioactive medicine 102 administered to the subject 101. Generally, the collimator for low energy is structured thinner in porous partition wall, smaller in pore size and greater in the number of pores than the collimator for high energy. Furthermore, of among the collimators for low and high energies, a plurality of type of collimators, e.g. general-purpose collimators and high-resolution collimators, can be employed in accordance with use purpose.

The gamma camera section 1 thus structured is to convert the gamma rays entered through the collimator into an electric signal and calculates a two-dimensional position (X, Y) and energy (Z) of the entered gamma rays. The gamma camera section 1 inputs an XY signal representative of a two-dimensional position to a gamma-ray count circuit 5 and a Z signal representative of an energy to the window circuits 2A, 2B, 2C and to the CPU 4.

In the case the Z signal inputted from the gamma camera section 1 represents an energy fallen within a collection window having a predetermined energy width, the window circuit notifies the fact in the form of one pulse signal to the gamma-ray count circuit 5. Here, in the FIG. 1 nuclear medical apparatus employs a TEW scheme in scattering-ray correction. In order to realize the TEW scheme, the window circuit of the FIG. 1 nuclear medical apparatus is constituted with three systems of the window circuits 2A, 2B, 2C. However, in the first embodiment, the structure for realizing the TEW scheme is not essentially required but scattering-ray correction may be implemented in another scheme than the TEW scheme.

The window circuit 2A is to generate one pulse signal in the case the Z signal, inputted from the gamma camera section 1, represents an energy fallen within the range of a main window (first collection window). The main window is set up at and around an energy (peak energy) at which the count on the radioisotope to collect is maximized. The peak energy is determined unambiguously in accordance with the nuclide to collect, e.g. $^{99m}$Tc has a peak energy of 140 keV.

Meanwhile, the window circuit 2B is to generate one pulse signal in the case the Z signal represents an energy fallen within the energy range of a sub-window (second collection window) adjacent to and on a lower energy side than the main window. Furthermore, the window circuit 2C is to generate one pulse signal in the case the Z signal represents an energy fallen within the energy range of a sub-window (third collection window) adjacent to and on a higher energy side than the main window.

Here, the first embodiment has one feature that the number of gamma rays is to be determined correctly by correcting in real time the effect of the gamma-ray collection efficiency changing from collimator to collimator and from energy to energy. For this purpose, the FIG. 1 nuclear medical apparatus has the collection-efficiency memory 3, the CPU 4 and the gamma-ray count circuit 5.

Figure 2:
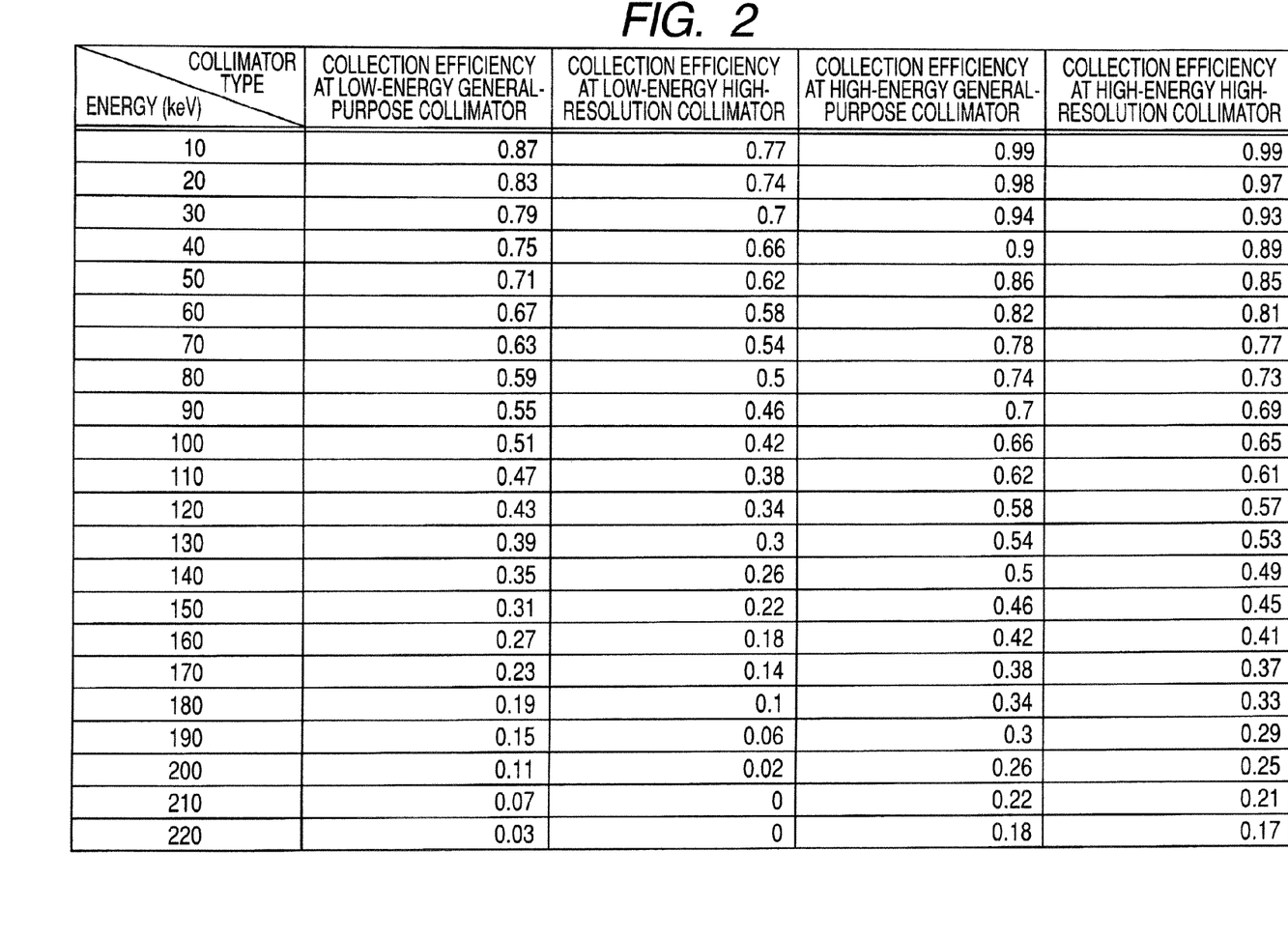
FIG. 2 is a figure showing an example of a collection efficiency table.

The collection-efficiency memory 3 is a memory to store a table of the collimators arranged on the gamma camera section 1 on a type-by-type basis and gamma-ray collection efficiencies on an energy-by-energy basis (hereinafter, referred to as a collection efficiency table). Collection efficiency is a value representing what count is measured as gamma rays when the gamma rays in an amount of one count have entered the gamma camera section 1. Such a collection efficiency table is exemplified in FIG. 2. In FIG. 2, there are shown, as collimator types, a low-energy general-purpose collimator, a low-energy high-resolution collimator, a high-energy general-purpose collimator and a high-energy high-resolution collimator. Incidentally, how to prepare such a collection efficiency table as in FIG. 2 will be detailed later.

The CPU 4 is to acquire from the collection efficiency memory 3 a collection efficiency corresponding to the collimator recognition information and Z signal notified from the gamma camera section 1, and notifies a reciprocal to the acquired collection efficiency to the gamma-ray count circuit 5.

Figure 3:
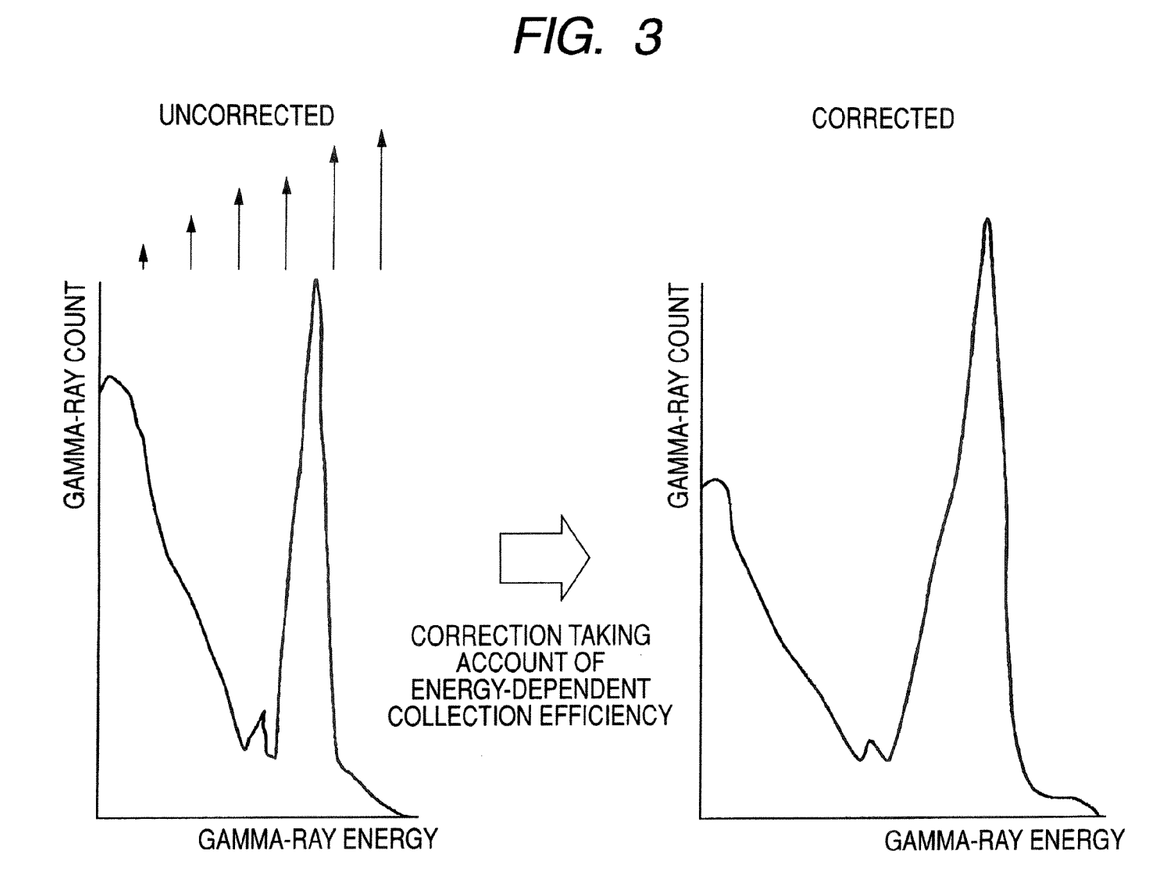
FIG. 3 is a figure showing a way of thinking taking account of energy-dependent collection efficiency.

Here, collection efficiency is a value representing what count is measured as gamma rays when the gamma rays in an amount of one count have entered the gamma camera section 1, as noted above. Accordingly, the count value of the gamma rays, actually entered the gamma camera section 1, can be considered as a reciprocal to the collection efficiency. If thinking so, by summing up the reciprocal to the collection efficiency corresponding to the energy the gamma rays possesses and the type of the collimator currently arranged each time one count of gamma rays is measured, the count value of gamma rays can be corrected by taking account of the collection efficiency relying upon energy as shown in FIG. 3.

Based on such a way of thinking, when receiving an XY signal from the gamma camera section 1, a pulse signal from the window circuit 2A and a reciprocal to collection efficiency from the CPU 4, the gamma-ray count circuit 5 sequentially adds the reciprocal to collection efficiency to a predetermined address of an image memory 6A which stores the two-dimensional position data, as represented by the XY signal. By such an operation, after an image-taking period, the count value of the gamma rays having an energy fallen within the main window is determined in a state corrected for the effect of collection efficiency on each point and on each energy, thus gathering a spatial distribution of the gamma-ray count values as image data.

When receiving an XY signal from the gamma camera section 1, a pulse signal from the window circuit 2B and a reciprocal to collection efficiency from the CPU 4, the gamma-ray count circuit 5 sequentially adds the reciprocal to collection efficiency to a predetermined address of an image memory 6B, which stores the two-dimensional position data, as represented by the XY signal. By such an operation, after an image-taking period, the count value of the gamma rays having an energy fallen within the sub-window adjacent to and on a lower energy side than the main window is determined in a state corrected for the effect of collection efficiency on each point and on each energy, thus gathering a spatial distribution of the gamma-ray count values as image data.

Furthermore, when receiving an XY signal from the gamma camera section 1, a pulse signal from the window circuit 2C and a reciprocal to collection efficiency from the CPU 4, the gamma-ray count circuit 5 sequentially adds the reciprocal to collection efficiency to a predetermined address of an image memory 6C which stores the two-dimensional position data, as represented by the XY signal. By such an operation, after an image-taking period, the count value of the gamma rays having an energy fallen within the sub-window adjacent to and on a higher energy side than the main window is determined in a state corrected for the effect of collection efficiency on each point and on each energy, thus gathering a spatial distribution of the gamma-ray count values as image data.

In the case there is an energy difference between a plurality of gamma rays collected in the gamma camera section 1, if those are measured equally as one count, errors result due to the difference in collimator's collection efficiency from energy to energy. For this reason, correction for count value is essentially required in taking account of energy-based collimator's collection efficiencies. Conventionally, it is a practice to measure gamma rays one count a time and multiply the reciprocal to collimator's collection efficiency on the finally obtained count value in a region concerned thereby correcting for the count value of gamma rays. However, this also is premised on the case the gamma rays to collect are thoroughly equal in energy within the region concerned. For this reason, in the case of collecting gamma rays having a plurality of energy distributions as in the Anger gamma camera for example, it is particularly effective to apply such an approach of correcting for count value each time one count of gamma rays is measured as explained in the present embodiment.

The count values gathered in the image memory 6A are supplied to the image processor 7A. The count values gathered in the image memory 6B are supplied to the image processor 7B. The count values gathered in the image memory 6C are supplied to the image processor 7C. The image processors 7A, 7B, 7C each perform, on the count value supplied, various corrections except for scattering-ray correction, e.g. energy correction, linearity correction for distortions at the peripheral edge of field-of-view, uniformity correction for sensitivity variations between the photoelectron multipliers and semiconductor elements the gamma camera section 1 possesses, and absorption correction for the count errors resulting from an uneven absorption of the living body.

Figure 4:
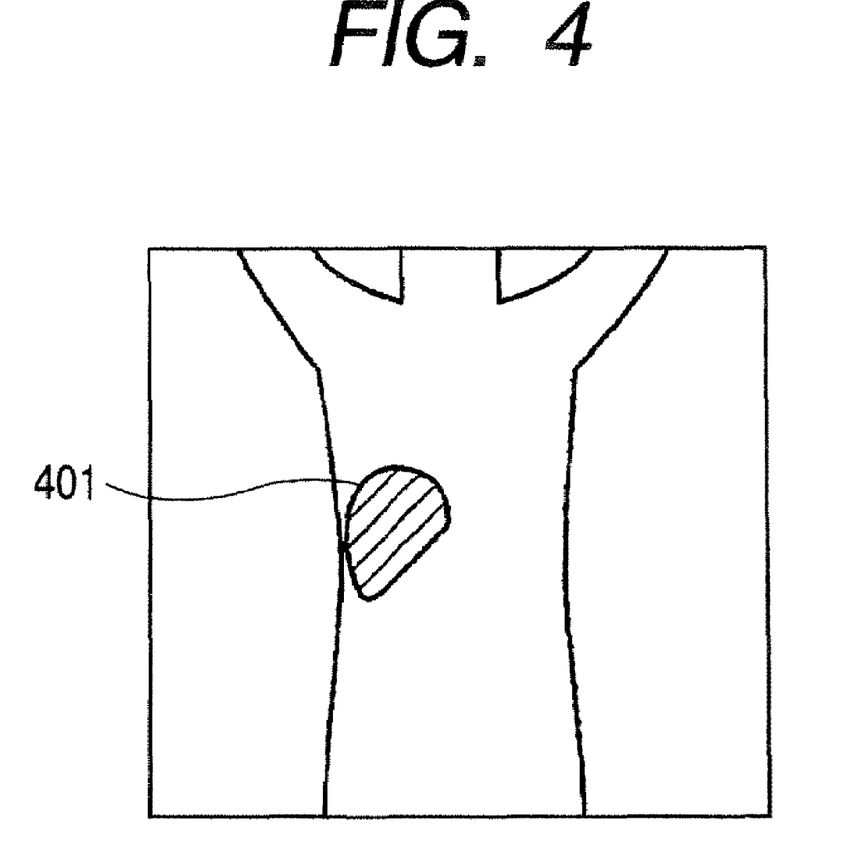
FIG. 4 is a figure showing an example of an image displayed on a display.

The scatter correction processor 8 is to correct for scattering rays according to the TEW scheme. A display 9 is to display an image whose pixel value is based on the count value, of the gamma rays in the main window, corrected by the scatter correction processor 8. This can display on the display 9 the location of a radioactive medicine administered to the subject, as an image as shown at reference numeral 401 in FIG. 4, depending upon the gamma rays given off from the subject.

Figure 5:
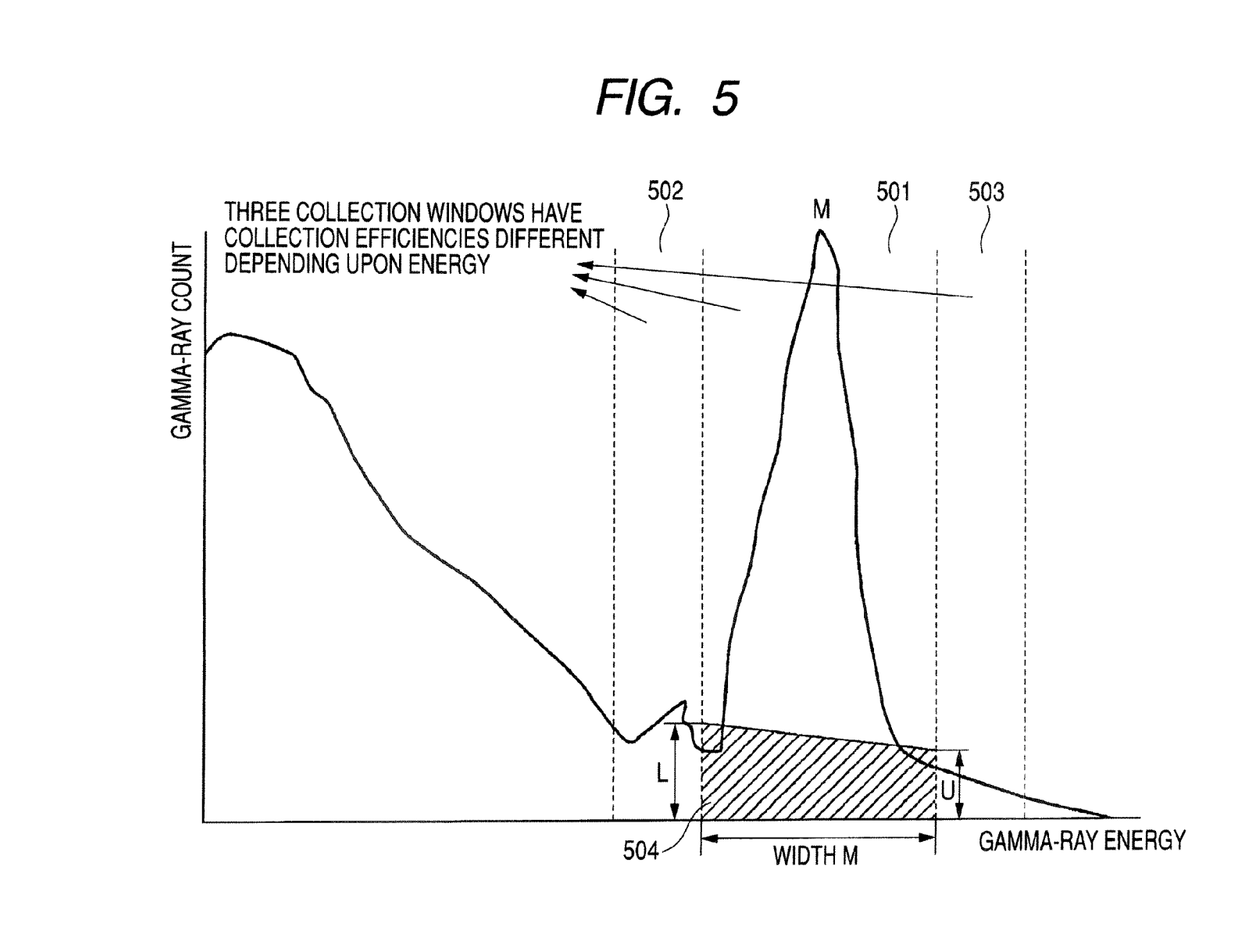
FIG. 5 is a figure for explaining the scattering-ray correction under a TEW scheme.

Referring to FIG. 5, explanation is now made briefly on the scattering-ray correction to be performed in the scatter correction processor 8. As shown in FIG. 5, the scattering-ray correction utilizing the TEW scheme is to determine a true count value in the main window by providing sub-windows 502, 503 on the lower-energy and higher-energy sides relative to the main window 501, estimating by trapezoidal approximation the scattering-ray amount (area of the trapezoidal region 504 shown in FIG. 5) in the main window 501 by use of the count values in the two sub-windows, and subtracting the estimated scattering-ray amount from the count value of the main window.

Provided that the mean count value in the lower-energy side sub-window 502 (i.e. the value that the output of the image memory 6B is divided by the energy width in the lower-energy side sub-window 502) is U, the mean count value in the higher-energy side sub-window 503 (i.e. the value that the output of the image memory 6C is divided by the energy width in the higher-energy side sub-window 503) is L, the total count value in the main window 501 (i.e. the output of the image memory 6A) is M and the energy width in he main window 501 is M width, then the gamma rays in the main window 501 has a true count value to be determined from the following:

$$\text{true count value} = M - (L+U) \times \text{width } M/2 \qquad \text{(Equation 1)}.$$

Here, the above M, L and U in (Equation 1) are respective count values in different energy collection windows. Namely, those collection windows have different collection efficiencies. However, in the first embodiment, prior to performing an arithmetic operation of (Equation 1), the count values in the respective collection windows are corrected by taking account of the effect of the collection efficiency changing from energy to energy. Thus, it is possible to improve the accuracy where scattering-ray correction has been done according to the TEW scheme.

Figure 6:
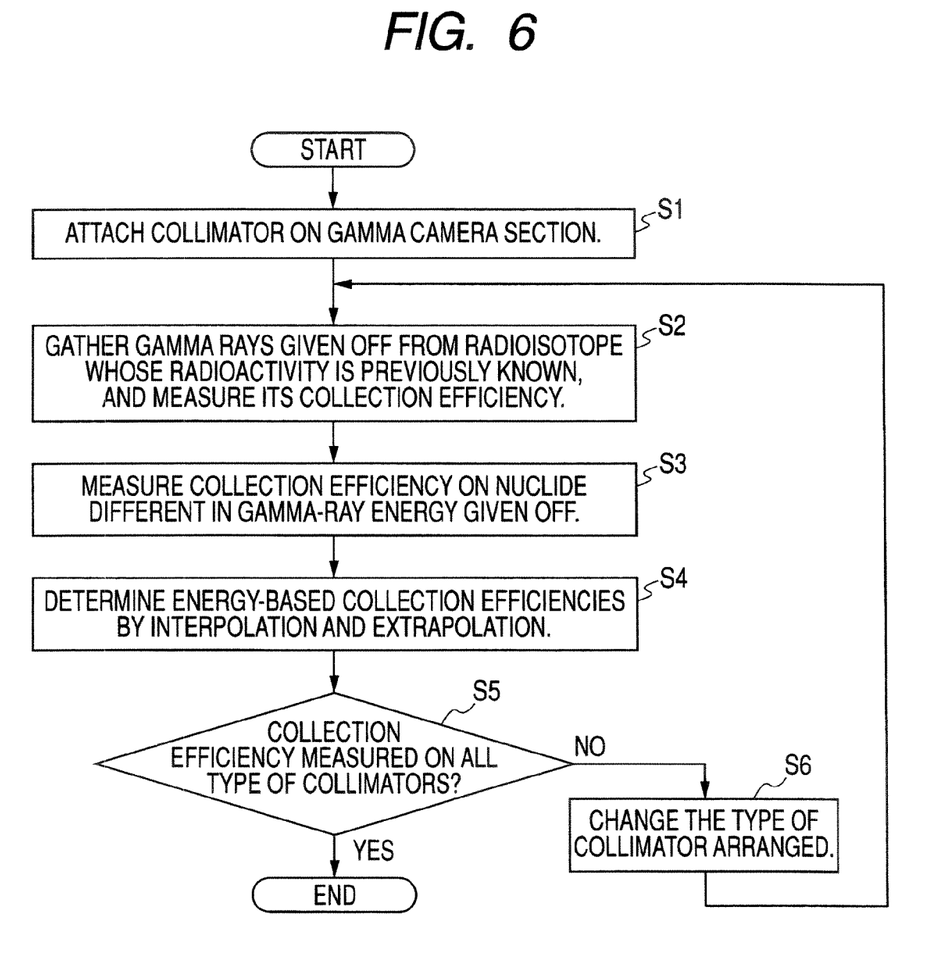
FIG. 6 is a flowchart showing a manner of preparing a collection efficiency table.

Referring to FIG. 6, explanation is now made on how to prepare a collection efficiency table to be stored in the collection efficiency memory 3. FIG. 6 is a flowchart showing a manner to prepare a collection efficiency table.

At first, a collimator, assumed to use, is arranged on the gamma camera section 1 (step S1). Then, the gamma rays, given off from a radioisotope whose radioactivity is known, are collected for a predetermined time through the gamma camera section 1. After the collection of gamma rays for the predetermined time, the collection efficiency at that time is calculated. The calculated collection efficiency is stored in the collection efficiency memory 3 by placing it corresponding to the type of the collimator currently arranged and the energy of gamma rays collected (step S2). Here, in case the radioactivity is known, it is possible to determine a count value of the gamma rays assumed to be collected in a predetermined time. Therefore, the collection efficiency can be determined by dividing the count value of the gamma rays actually collected in a measurement for a predetermined time by the count value of gamma rays determined by the radioactivity.

Then, collection efficiency measurement is similarly made on a plurality of nuclides that are different in the energy of gamma rays given off (step S3). After the collection efficiency measurement on the plurality of nuclides, interpolation and extrapolation are performed on the plurality of energy-based collection efficiencies, thereby determining a collection efficiency for a desired energy (step S4).

After the step S4, it is determined whether or not collection efficiency measurement was made on all the collimators assumed for use (step S5). In the case collection efficiency measurement was not done on all the collimators in the determination of step S5, another collimator is attached to the gamma camera section 1 (step S6) and then the process returns to step S2 where collection efficiency measurement is performed on the other collimator. Meanwhile, in the case collection efficiency measurement was done on all the collimators in the determination of step S5, the preparation of a collection efficiency table is ended.

As explained so far, the first embodiment can provide a more quantitative image by correcting the gamma-ray count value through taking account of the effect of collimator-based energy-dependent collection efficiency. Particularly, in the field of molecular imaging actively studied in the recent, it is significantly emphasized to quantitatively analyze the distribution and quantity of protein in diagnosing the presence or absence of and spread status of a cancer tissue. Namely, it is known that cancer tissue produces a certain particular protein. In case it is separated from other proteins and specified of aggregated point and exact aggregation amount, obtained is so-called staging information representative of a cancer-tissue progression degree. According to the first embodiment to perform a count correction through taking account of the effect of collection efficiency, quantification can be made on the protein unique to cancer tissue in the body, thus making a diagnosis quantitatively. In addition, it is possible to improve the accuracy of scattering-ray correction according to the TEW scheme, etc.

Here, the FIG. 2 collection efficiency table is one example, i.e. storage may be with collection efficiencies other than the collimators shown in FIG. 2. Meanwhile, although the collection efficiency itself was stored in FIG. 2, storage may be with a reciprocal to collection efficiency.

SECOND EMBODIMENT

Figure 7:
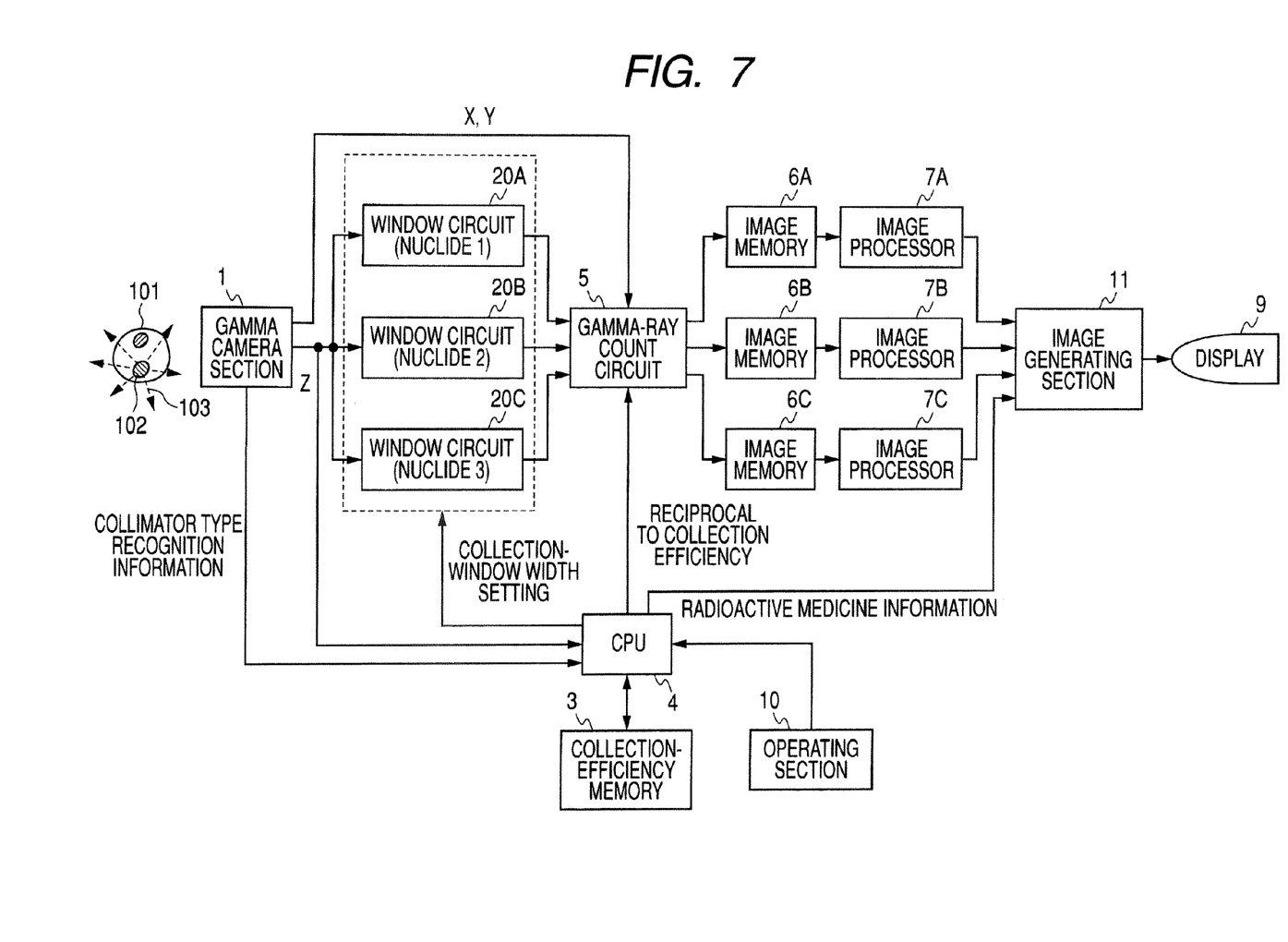
FIG. 7 is a diagram showing the main arrangement of a nuclear medical apparatus according to a second embodiment of the invention.

A second embodiment in the invention will now be explained. The second embodiment in the invention is an example that the invention is applied to a nuclear medical apparatus capable of detecting a plurality of radioisotopes simultaneously. FIG. 7 shows a main arrangement of a nuclear medical apparatus of the second embodiment. Incidentally, the FIG. 7 arrangement is an example of a nuclear medical apparatus capable of detecting three types of nuclides. The second embodiment is provided with window circuits 20A, 20B, 20C in place of the window circuits 2A, 2B, 2C of the first embodiment, as shown in FIG. 7. The window circuits 20A, 20B, 20C are provided to separate the gamma rays from the nuclides (hereinafter, referred to as nuclides 1, 2 and 3) radiating gamma rays different in energy peak.

Namely, the window circuit 20A is to generate one pulse signal in the case the Z signal, inputted from the gamma camera section 1, represents an energy fallen within the range of the collection window including the peak energy of nuclide 1. The window circuit 20B is to generate one pulse signal in the case the Z signal represents an energy fallen within the range of the collection window including the peak energy of nuclide 2 different in peak energy from nuclide 1. Furthermore, the window circuit 20C is to generate one pulse signal in the case the Z signal represents an energy fallen within the range of the collection window including the peak energy of nuclide 3 different in peak energy from nuclide 1. Incidentally, the window circuits 20A, 20B, 20C can be desirably set with collection windows respectively.

Here, FIG. 7 is omitted of the structure for making a scattering-ray correction according to the TEW scheme, in order to simplify the explanation. Where to enable scattering-ray correction, it is satisfactory to provide window circuits for two, or higher and lower energy, sub-windows on each of the window circuits 20A, 20B, 29C and to provide a scatter correction processor 8 in the following stage to the image processors 7A, 7B, 7C. Meanwhile, in order to enable detection of nuclides greater in the number than three types, it is satisfactorily to increase the number of the window circuits, image memories and image processors correspondingly.

In FIG. 7, there are also provided an operating section 10 for the physician, etc. to make various settings, such as collection window setting to the nuclear medical apparatus, and an image generating part 11 for generating predetermined image data from the image processed by the image processors 7A, 7B, 7C.

Figure 8:
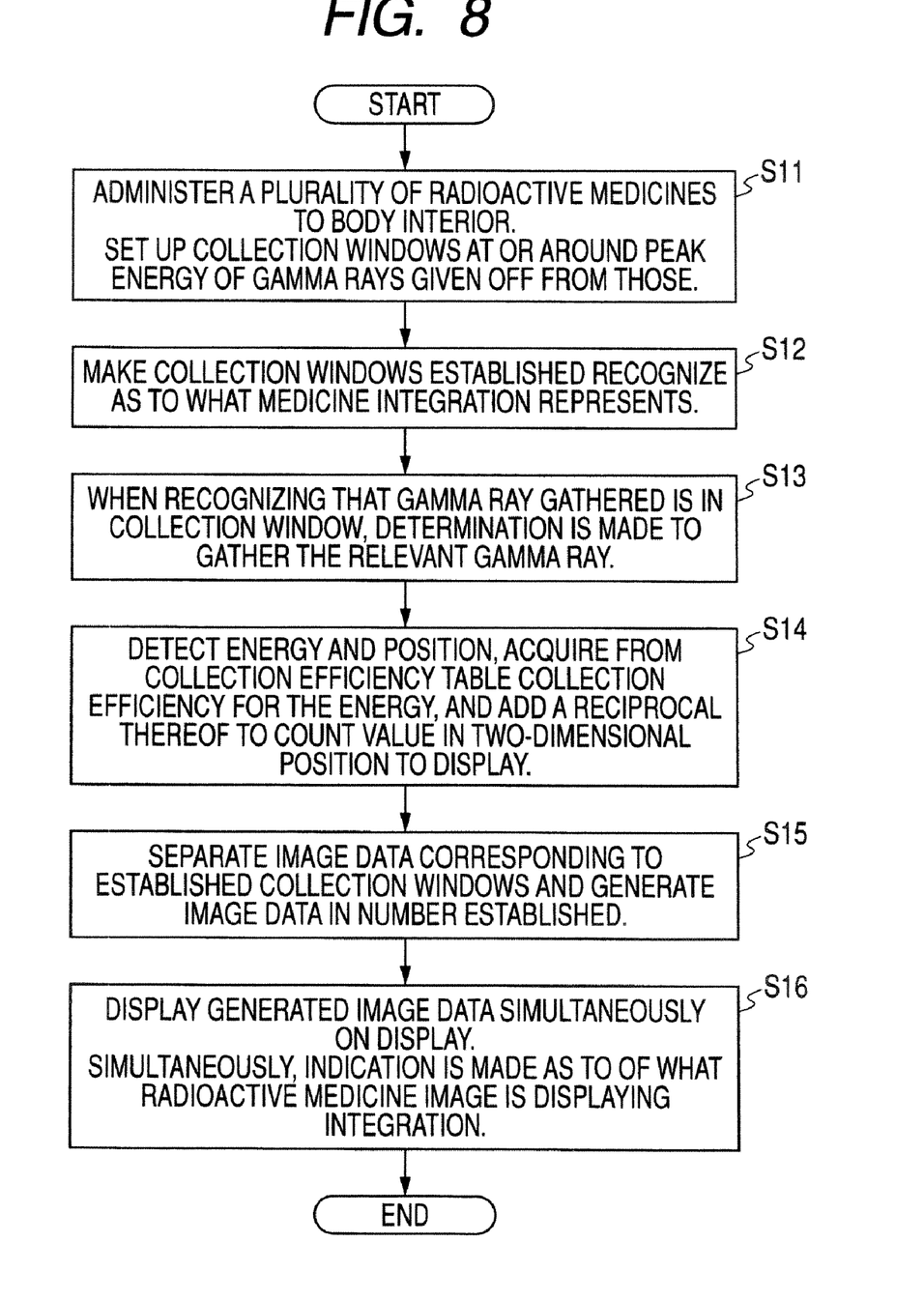
FIG. 8 is a flowchart for explaining the operation of the nuclear medical apparatus according to the second embodiment of the invention.
Figure 9:
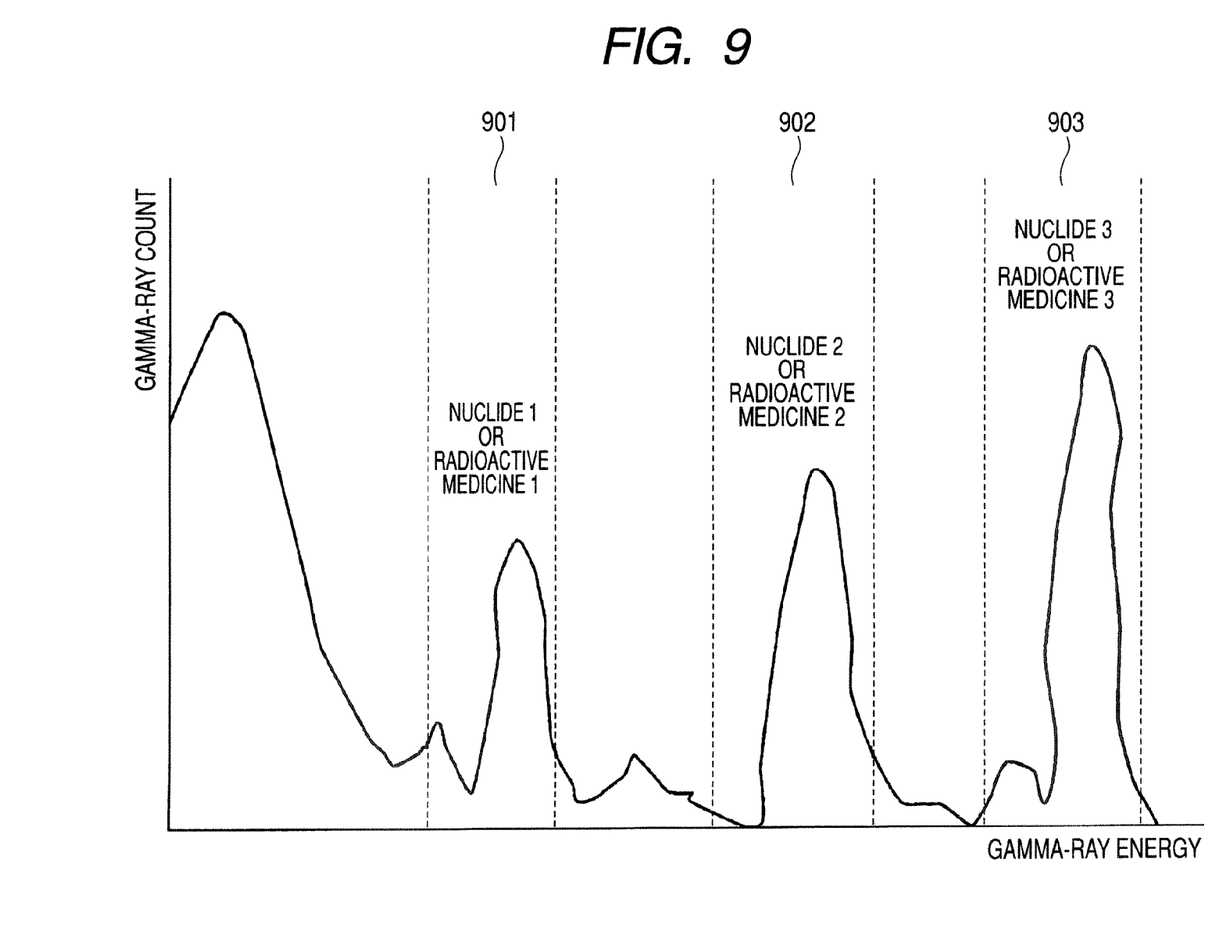
FIG. 9 is a figure for explaining a collection-window setting technique in the case a plurality of radioisotopes are administered.

Referring to a flowchart of FIG. 8, explanation is now made on the operation of the nuclear medical apparatus of the second embodiment. At first, the physician, etc. administer a plurality of radioactive medicines to the subject. It is herein assumed, as an example, that administered were radioactive medicine 1 containing nuclide 1, radioactive medicine 2 containing nuclide 2 and radioactive medicine 3 containing nuclide 3. Thereafter, the window circuits 20A, 20B, 20C are respectively set with collection windows through the operating section 10 so that gamma rays can be detected from the nuclides contained in the respective radioactive medicines (step S11). This sets the window circuits with collection window widths through the CPU 4. The collection windows are each set about the peak energy of the nuclide to be measured, as shown at reference numerals 901, 902, 903 in FIG. 9. After establishing the collection windows, setting is made at step S11 through the operating section 10 to what radioactive medicines the collection windows established respectively correspond (step S12). This recognizes the names of the radioactive medicines by means of the CPU 4.

After the above process, started is a detection of the gamma rays of from the radioisotope by means of the nuclear medical apparatus. In the case the gamma rays, detected through the gamma camera section 1, has an energy fallen within any of the collection windows of the window circuits 20A, 20B, 20C, the relevant window circuit determines to collect the gamma rays and notifies the fact by means of one pulse signal to the gamma-ray count circuit 5 (step S13). Meanwhile, the CPU 4 acquires a collection efficiency from the collection efficiency memory 3 according to the collimator recognition information and the Z signal representative of an energy of the gamma ray detected at that time, and notifies it to the gamma-ray count circuit 5. The collection-efficiency acquisition operation is similar to that explained in the first embodiment.

When receiving an XY signal from the gamma camera section 1, a pulse signal from the window circuit and a collection efficiency from the CPU 4, the gamma-ray count circuit 5 sequentially adds the reciprocal to collection efficiency to a predetermined address of the corresponding image memory, thereby determining a count value of gamma rays (step S14). This stores a count value of the gamma rays as to nuclide 1 in the image memory 6A, a count value of the gamma rays as to nuclide 2 in the image memory 6B and a count value of the gamma rays as to nuclide 3 in the image memory 6C.

Figure 10A:
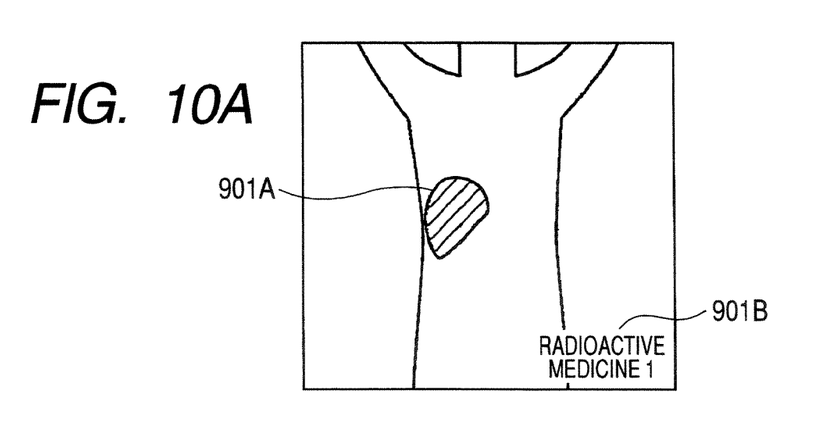
FIGS. 10A, 10B and 10C are figures explaining an example of an image generated by the image generating section in the second embodiment.
Figure 10B:
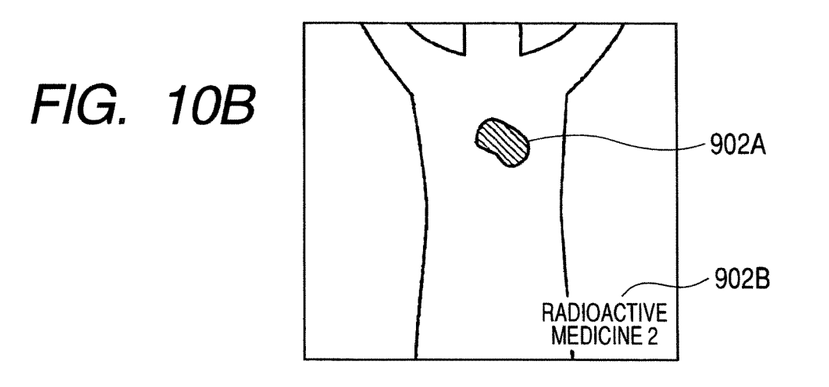
Figure 10C:
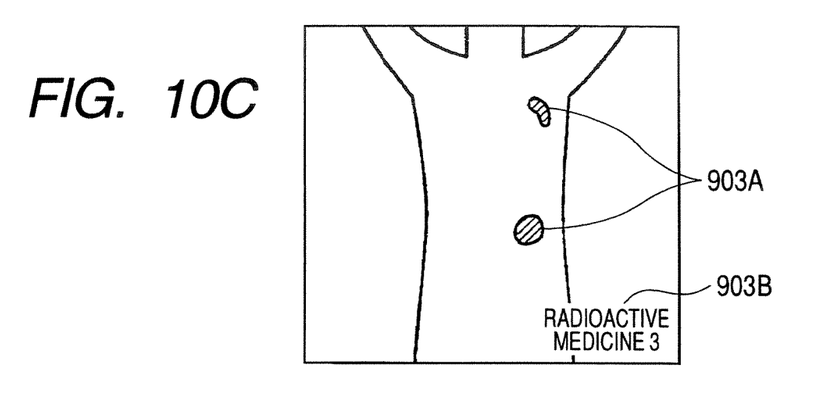

The image processors 7A, 7B, 7C each perform a correction as noted before on the gamma-ray count value stored in the corresponding image memory. The image generating section 11 generates an image as shown in FIG. 10A from the gamma-ray count value corrected in the image processor 7A, an image as shown in FIG. 10B from the gamma-ray count value corrected in the image processor 7B and an image as shown in FIG. 10C from the gamma-ray count value corrected in the image processor 7C (step S15). Thereafter, the display 9 makes a display of the three images of data thus generated (step S16). In such a case, it is satisfactory to simultaneously display three images by dividing one screen of the display 9 into three parts. Otherwise, the display 9 may display thereon the images shown in FIGS. 10A-10C one by one wherein the image being displayed on the display 9 can be switched over by operating the operating section 10 or so.

In this manner, because the radioactive medicines containing radioisotopes different in radiation energy of gamma rays can be displayed separately as shown at reference numerals 901A, 901B and 903A respectively in FIGS. 10A, 10B and 10C, the physician, etc. is allowed to easily visually discriminate at what points of the subject were absorbed a plurality of radioactive medicines administered to the subject. Incidentally, in making a display as in FIGS. 10A, 10B and 10C, it is preferred to indicate as to which radioactive medicine each image is concerned with depending upon the radioactive medicine information recognized by the CPU 4, as shown at reference numerals 901B, 902B, 903B respectively in FIGS. 10A, 10B, 10C for example. This makes apparent the relevance of each image to the radioactive medicine. In such a case, display may be with a protein name for which the radioactive medicine is used.

A modification to the second embodiment is now explained. The modification is an example to display, on the display 9, a combination of the image generated by the image processor 7A, the image generated by the image processor 7B and the image generated by the image processor 7C, differently from FIG. 10.

Figure 11:
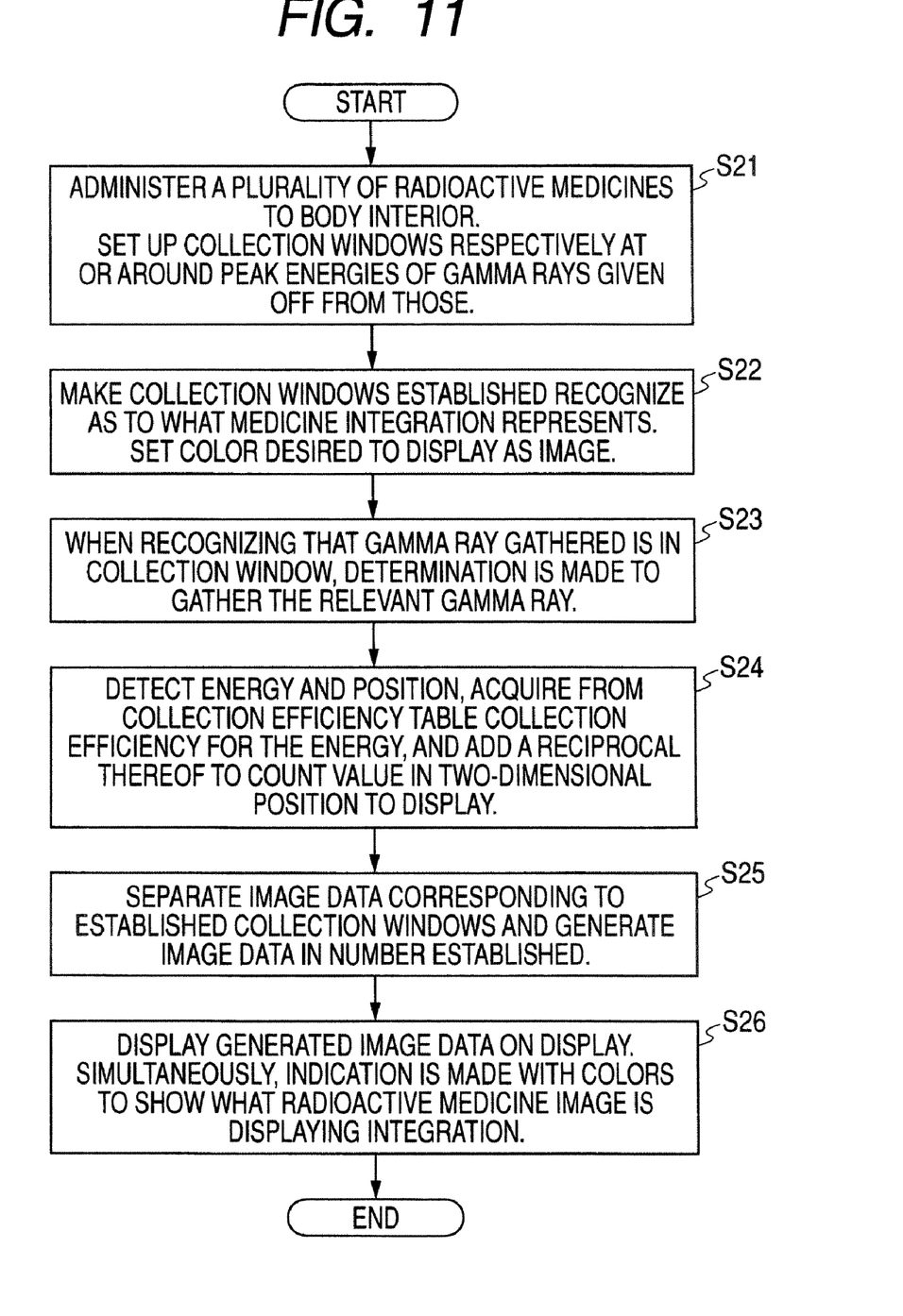
FIG. 11 is a flowchart for explaining the operation of the nuclear medical apparatus according to a modification to the second embodiment.

Referring to a flowchart of FIG. 11, explanation is now made on the operation of the nuclear medical apparatus of the modification. At first, the physician, etc. administer a plurality of radioactive medicines (radioactive medicines 1, 2 and 3) to the subject. Thereafter, the window circuits 20A, 20B, 20C are respectively set with collection windows through the operating section 10 so that gamma rays can be detected from the nuclides respectively contained in the radioactive medicines (step S21). After establishing the collection windows, setting is made concerning to which radioactive medicines the collection windows established respectively correspond, as well as the colors for displaying the respective radioactive medicines as images (step S22).

After the above process, started is a detection of the gamma rays of from the radioisotopes by means of the present nuclear medical apparatus. Due to this, in the case the gamma rays detected through the gamma camera section 1 has an energy fallen within any of the collection windows of the window circuits 20A, 20B, 20C, the relevant window circuit determines to gather the gamma rays and notifies the fact by means of one pulse signal to the gamma-ray count circuit 5 (step S23). Meanwhile, the CPU 4 acquires a collection efficiency from the collection efficiency memory 3 according to the collimator recognition information and the Z signal representative of an energy of the gamma ray detected at that time, and notifies it to the gamma-ray count circuit 5.

When receiving an XY signal from the gamma camera section 1, a pulse signal from the window circuit and a collection efficiency from the CPU 4, the gamma-ray count circuit 5 sequentially adds the reciprocal to collection efficiency to a predetermined address of the corresponding image memory, thereby determining a count value of gamma rays (step S24). This stores a count value of the gamma rays as to nuclide 1 in the image memory 6A, a count value of the gamma rays as to nuclide 2 in the image memory 6B and a count value of the gamma rays as to nuclide 3 in the image memory 6C.

Figure 12:
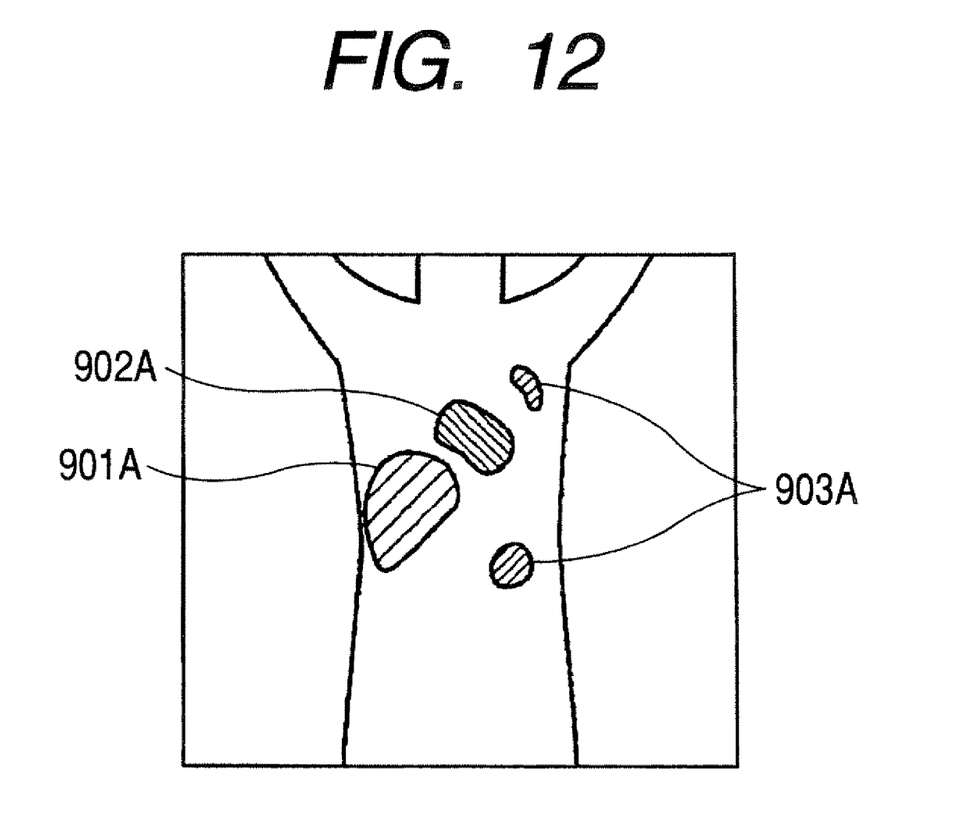
FIG. 12 is a figure showing an example of a combined image generated by the image generating section in the modification to the second embodiment.

The image processors 7A, 7B, 7C each perform a correction as noted before on the gamma-ray count value stored in the corresponding image memory. The image generating section 11 generates three sheets of image data as shown in FIGS. 10A, 10B, 10C from the gamma-ray count values corrected in the image processors 7A, 7B, 7C (step S25). The image generating section 11 combines three sheets of image data together and forms an image as shown in FIG. 12. In this case, the image generating section 11 separates the colors respectively for the radioactive medicines. Thereafter, the display 9 makes a display of the combined image produced in the image generating section 11 (step S26). Incidentally, in displaying the FIG. 12 image, indication may be given as to what color designates what radioactive medicine.

As explained so far, the second embodiment allows for correctly separating the plurality of radioactive medicines administered to the body interior and displaying those with visual discrimination, thus making it possible to provide an image that is easy to know the qualitativeness of a plurality of medicines.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A nuclear medical apparatus for obtaining a distribution of a radioisotope in a subject by administering to the subject a radioactive medicine containing a radioisotope, comprising:
    a gamma-ray detecting section configured to detect gamma rays given off from the radioisotope;
    a count section configured to count the gamma rays detected by the gamma-ray detecting section; and
    a correcting section configured to add a reciprocal of a collection efficiency, which is determined according to the gamma-ray detecting section and an energy the gamma rays possess, to a count taken at the counting section each time the gamma rays are gathered by the gamma-ray detection section.

2. A nuclear medical apparatus comprising:
    a gamma-ray detecting section configured to detect gamma rays given off from a radioisotope contained in a radioactive medicine administered to a subject and to determine an incident site of the gamma rays and an energy the gamma rays possess;
    a gamma-ray collecting section configured to gather the gamma rays, when gamma rays detected at the gamma-ray detecting section have an energy within a predetermined collection window;
    an output section configured to output a value commensurate with a collection efficiency of the gamma rays determined according to a type of the gamma-ray detecting section and an energy the gamma rays possess, the output section configured to output a reciprocal of the collection efficiency as a value commensurate with the collection efficiency;
    a gamma-ray count section configured to determine a count value of the gamma rays that have entered the gamma-ray detecting section depending upon the value commensurate with a collection efficiency outputted from the output section, when gamma rays are gathered in the gamma-ray collecting section, and to add the reciprocal of the collection efficiency to the count value each time gamma rays are gathered by the gamma-ray collecting section, thereby determining the count value of gamma rays; and
    a display section configured to display an image based on the determined count value of gamma rays.

3. A nuclear medical apparatus according to claim 2, wherein the gamma-ray detecting section includes a collimator that regulates an incident angle of gamma rays from the radioisotope.

4. A nuclear medical apparatus according to claim 2, further comprising:
    a scatter correcting section configured to make a scattering ray correction depending upon separately determined count values of gamma rays prior to displaying an image on the display section,
    wherein the gamma-ray collecting section includes
    a first window circuit that gathers gamma rays, when gamma rays detected at the gamma-ray detecting section have an energy within a first collection window,
    a second window circuit that gathers gamma rays, when gamma rays detected at the gamma-ray detecting section have an energy within a second collection window adjacent to and on a lower energy side than the first collection window, and
    a third window circuit that gathers gamma rays, when gamma rays detected at the gamma-ray detecting section have an energy within a third collection window adjacent to and on a higher energy side than the first collection window,
    wherein the gamma-ray count section determines the separately determined count values of the gamma rays which are respectively gathered in the first, second and third window circuits, separately and on an incident-site basis.

5. A nuclear medical apparatus comprising:
    a gamma-ray detecting section configured to detect gamma rays given off from radioisotopes different in energy peaks and respectively contained in a plurality of radioactive medicines administered to a subject, and to determine an incident site of the gamma rays and an energy the gamma rays possess;
    a gamma-ray collecting section configured to gather the detected gamma rays on each of the radioisotopes;
    an output section that outputs a value commensurate with a collection efficiency of gamma rays determined by the gamma-ray detecting section according to a type of the gamma-ray detecting section and an energy the gamma rays possesses, and
    a gamma-ray count section that determines a count value of gamma rays detected by the gamma-ray detecting section on each of the incident sites and of the radioisotopes depending upon the value commensurate with a collection efficiency outputted from the output section, when the gamma rays are gathered in the gamma-ray collecting section, a display section configured to display an image for each of the radioisotopes gathered, display the image depending upon the count value of gamma rays on each of the radioisotopes counted, and output a reciprocal of the collection efficiency as a value commensurate with the collection efficiency, wherein the gamma-ray count section is configured to add the reciprocal of the collection efficiency to the count value each time gamma rays are gathered by the gamma-ray collecting section, thereby determining the count value of gamma rays.

6. A nuclear medical apparatus according to claim 5, wherein the display section is configured to display a plurality of images separately and on a radioisotope-by-radioisotope basis.

7. A nuclear medical apparatus according to claim 6, wherein the display section is configured to display, together with the image, at least any of a name of the radioactive medicine administered to the subject and a name of a protein to image by utilization of the radioactive medicine.

8. A nuclear medical apparatus according to claim 5, wherein the display section is configured to display the image with colors on a radioisotope-by-radioisotope basis.

* * * * *